(12) United States Patent
Ghaderi et al.

(10) Patent No.: US 11,426,439 B2
(45) Date of Patent: Aug. 30, 2022

(54) NUTRITIONAL PRODUCT AND METHOD OF USING IT

(71) Applicant: ProPhase Labs, Inc., Doylestown, PA (US)

(72) Inventors: Raouf Ghaderi, Flemington, NJ (US); Ted Karkus, Woodmere, NY (US)

(73) Assignee: ProPhase Labs, Inc., Doylestown, PA (US)

( * ) Notice: Subject to any disclaimer, the term of this patent is extended or adjusted under 35 U.S.C. 154(b) by 0 days.

(21) Appl. No.: 16/982,145

(22) PCT Filed: Mar. 19, 2019

(86) PCT No.: PCT/US2019/022869
§ 371 (c)(1),
(2) Date: Sep. 18, 2020

(87) PCT Pub. No.: WO2019/183028
PCT Pub. Date: Sep. 26, 2019

(65) Prior Publication Data
US 2021/0069274 A1    Mar. 11, 2021

Related U.S. Application Data

(60) Provisional application No. 62/645,456, filed on Mar. 20, 2018.

(51) Int. Cl.
| | |
|---|---|
| *A61K 36/41* | (2006.01) |
| *A23L 33/175* | (2016.01) |
| *A23L 33/105* | (2016.01) |
| *A23L 33/15* | (2016.01) |
| *A61K 9/48* | (2006.01) |
| *A61K 31/198* | (2006.01) |
| *A61K 31/475* | (2006.01) |
| *A61K 31/714* | (2006.01) |
| *A61K 36/15* | (2006.01) |
| *A61K 36/185* | (2006.01) |
| *A61K 36/21* | (2006.01) |
| *A61K 36/258* | (2006.01) |
| *A61K 36/48* | (2006.01) |
| *A61K 36/53* | (2006.01) |
| *A61K 36/71* | (2006.01) |
| *A61K 36/9068* | (2006.01) |

(52) U.S. Cl.
CPC ............ *A61K 36/41* (2013.01); *A23L 33/105* (2016.08); *A23L 33/15* (2016.08); *A23L 33/175* (2016.08); *A61K 9/48* (2013.01); *A61K 31/198* (2013.01); *A61K 31/475* (2013.01); *A61K 31/714* (2013.01); *A61K 36/15* (2013.01); *A61K 36/185* (2013.01); *A61K 36/21* (2013.01); *A61K 36/258* (2013.01); *A61K 36/48* (2013.01); *A61K 36/53* (2013.01); *A61K 36/71* (2013.01); *A61K 36/9068* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 4,698,360 A | 10/1987 | Masquelier | |
| 5,494,668 A | 2/1996 | Patwardhan | |
| 6,368,640 B1 | 4/2002 | Wuh et al. | |
| 8,217,165 B2 * | 7/2012 | Goel | A61K 36/48 536/128 |
| 2011/0144044 A1 * | 6/2011 | Kichuk | A61K 31/715 514/26 |
| 2013/0018061 A1 | 1/2013 | Bashir et al. | |
| 2013/0280367 A1 | 10/2013 | Bashir et al. | |
| 2015/0110758 A1 | 4/2015 | Amin | |
| 2015/0352172 A1 * | 12/2015 | Gokaraju | A61P 43/00 424/739 |
| 2016/0303177 A1 | 10/2016 | Bailey | |
| 2017/0348235 A1 | 12/2017 | White | |

FOREIGN PATENT DOCUMENTS

CA    2582784 A1    10/2007

OTHER PUBLICATIONS

International Search Report and Written Opinion for corresponding International application No. PCT/US2019/022869; dated Jun. 28, 2019 (9 pages).
Avalos-Soriano, Anaguiven, et al. "4-Hydroxyisoleucine from fenugreek (Trigonella foenum-graecum): effects on insulin resistance associated with obesity." Molecules 21.11 (2016): 1596-1607.
Hung, Shao Kang, et al. "The effectiveness and efficacy of *Rhodiola rosea* L.: a systematic review of randomized clinical trials." Phytomedicine 18.4 (2011): 235-244.
Parisi, A., et al. "Effects of chronic Rhodiola Rosea supplementation on sport performance and antioxidant capacity in trained male: preliminary results." Journal of Sports Medicine and Physical Fitness 50.1 (2010): 57-63.

(Continued)

*Primary Examiner* — Susan Hoffman
(74) *Attorney, Agent, or Firm* — Mendelsohn Dunleavy, P.C.

(57) ABSTRACT

A nutritional product for improving performance during physical activity and a method of using the nutritional product to improve performance during activity. The nutritional product contains *Rhodiola* root extract, French pine extract, *Pulsatilla vulgaris* extract, ginger extract, yohimbe extract, *Ginseng* extract, *Coleus forskohlii* extract, vitamin B12, red beet extract, L-Arginine NO3, tongkat ali, a combination of Fenugreek fenugreek A and Fenugreek fenugreek B, and *Tribulus terrestris* extract. Also described are methods for improving a user's physical activity performance employing the nutritional products.

20 Claims, No Drawings

(56) References Cited

OTHER PUBLICATIONS

Vinciguerra, G., et al. "Evaluation of the effects of supplementation with Pycnogenol® on fitness in normal subjects with the Army Physical Fitness Test and in performances of athletes in the 100-minute triathlon." The Journal of Sports Medicine and Physical Fitness 53.6 (2013): 644-654.

* cited by examiner

NUTRITIONAL PRODUCT AND METHOD OF USING IT

BACKGROUND OF THE INVENTION

A. Field of the Invention

The present invention relates to a nutritional product and method of using it. The nutritional product is designed to be ingested by a user prior to exercise to increase the energy and endurance of the user during exercise.

B. Background

Exercise is promoted as having a significant impact on a person's overall health and well-being. Individuals, serious athletes, as well as those exercising for fun, or a healthy lifestyle, often seek methods to improve exercise performance. Various nutritional supplements have been developed in an attempt to increase performance during exercise and enhance the ability to recover from exercise. The nutritional supplements may be designed to be taken pre-workout, during exercise, or during recovery. Nutritional supplements taken prior to exercise often focus on supplying carbohydrates in an attempt to maintain proper fueling during exercise. Other "pre-workout" supplements may contain amino acids, caffeine, herbal extracts, and protein supplements to support and enhance cardiovascular and muscular health during and after exercise.

Caffeine, in the form of energy drinks and coffee is commonly used pre-exercise as a supplement for enhancing performance. Caffeine is known to mobilize fat stores and encourage working muscles to use fat as a fuel, which results in less use of glycogen stores in muscles allowing a user to exercise for a longer time before exhaustion. Additionally, in studies asking participants to rate their level of perceived exertion, often those that have ingested caffeine prior to exercise report lower levels of exertion.

However, the use of caffeine comes with potential side effects such as increased heart rate, increased body temperature, a diuretic effect, diarrhea, and/or abdominal cramping. Moreover, the potential combination of dehydration and cramping caused by caffeine can have substantial detrimental effects on exercise performance.

U.S. Patent Application Publication No. 2013/0018061 teaches a nutritional supplement combining caffeine and L-theanine. The supplement is taken pre-workout and is said to be particularly beneficial for those that have developed a tolerance to caffeine. However, this publication does not address the side-effects that may be caused by caffeine.

Various herbal extracts that have been used for extended periods of time to treat ailments have shown potential benefits to overall health of user, as well as potentially providing physiological effects that would enhance performance during exercise.

*Rhodiola* Root Extract (*Rhodiola rosea*)

*Rhodiola rosea* is a plant in the *Rhodiola* genera (Crassulaceae family). *Rhodiola* has traditionally been used as an anti-fatigue agent and adaptogen compound, and has been shown to reduce the effects of prolonged and minor physical exhaustion that results in fatigue. One study using *Rhodiola* supplementation (170 mg daily for 4 weeks) noted a reduced fatty acid circulating level during a $VO_2$ max test without significantly affecting glucose, which was associated with increased antioxidative parameters in serum and less biomarkers associated with muscle damage. Parisi A, et al "Effects of chronic *Rhodiola rosea* supplementation on sport performance and antioxidant capacity in trained male: preliminary results." *J Sports Med Phys Fitness*. (2010). https://www.ncbi.nlm.nih.gov/pubmed/20308973. In this same study, lactate levels were also reduced after exercise. Additionally, one meta-analysis has assessed the interaction of *Rhodiola* supplementation on physical performance or physical fatigue, and determined that it may have beneficial effects on physical performance, mental performance, and certain mental health conditions. Hung S K, Perry R, Ernst E. "The effectiveness and efficacy of *Rhodiola rosea* L.: a systematic review of randomized clinical trials." *Phytomedicine*. (2011). https://www.ncbi.nlm.nih.gov/pubmed/21036578

French Pine Extract (*Pinus pinaster*)

Extracts of pine bark have been used to treat several different ailments. In 1534, French explorer Jacques Cartier and his crew are believed to have used extract from pine trees to treat scurvy. Further, extract from the French Maritime Pine has been shown to provide improved fitness performance. A study of triathletes, and athletes taking the Army Physical Fitness test showed that with proper hydration, good training and nutritional attention the extract of French pine may improve training and high levels performance in sports such as the triathlon. Vinciguerra, G. et al., "Evaluation of the effects of supplementation with Pycnogenol® on fitness in normal subjects with the Army Physical Fitness Test and in performances of athletes in the 100-minute triathlon." *J Sports Med Phys Fitness.*, 53(6):644-54 (December 2013). https://www.ncbi.nlm.nih.gov/pubmed/24247188.

*Pulsatilla vulgaris* Extract

*Pulsatilla*, also known as the Pasque flower, has been used in the form of a homeopathic medication to treat specific ailments. *Pulsatilla* is considered effective in lessening arterial stress, expanding the pupils and reducing respiration. The use of live *Pulsatilla* is known to be toxic, but when the dried plant is used in appropriate and very small doses, it does not appear to cause side effects.

Ginger Extract (*Zingiber officinale*)

Chinese medical texts from the fourth century B.C. suggest that ginger is effective in treating nausea, diarrhea, stomachaches, cholera, toothaches, bleeding, and rheumatism. Ginger was later used by Chinese herbalists to treat a variety of respiratory conditions, including coughs and the early stages of colds.

Ginger's modern use dates back to the early 1880s, when a scientist named D. Mowrey noticed that ginger-filled capsules reduced his nausea during an episode of flu. Inspired by this, he performed the first double-blind study of ginger. Germany's Commission E subsequently approved ginger as a treatment for indigestion and motion sickness. Ginger has become widely accepted as a treatment for nausea.

Ginger gives relief from muscular discomfort and pain. It inhibits prostaglandin and leukotriene biosynthesis and histamine release. Thus, it acts as an anti-inflammatory as well as an antacid agent. It is a dual inhibitor of the lipoxigenase and cycloxigenase system. Ginger contains 1-4% essential oil (oleoresin). Used alone fresh Ginger is required to be used in substantially high doses (50 grams daily), which is not only inconvenient but can act as an irritant to the gastric mucosa. In dry form for any significant results, 7 to 10 grams of dry ginger powder has to be taken daily. These therapeutic doses of ginger are extremely inconvenient for the patient and affect patient compliance on a daily basis. (See Potwardhan, U.S. Pat. No. 5,494,668.)

Yohimbe Extract (*Pausinystalia johimbe*)

Yohimbe extract comes from the inner bark of West African evergreen trees called *Pausinystalia johimbe*. The bark of these trees has been used in some western African nations as a supplement to provide sexual enhancement. Yohimbe has also been used to help build muscle, improve sexual function, reduce anxiety, elevate mood, and prevent heart attacks.

Ginseng

Ginseng in one species of plants belonging to the *Panax* genus of the family Araliaceae. Each of the species known as *Ginseng* is characterized by the presence of ginsenosides and gintonin. *Ginseng* has been used in traditional Chinese medicine as an overall wellness supplement. Specific uses for *Ginseng* include, boosting the immune system, improving heart health, treating diabetes, increasing energy, decreasing stress, and treating impotence.

Coleus forskolii

*Coleus forskolii* is a plant native to India. Plants of the *Coleus* species have been used as an herbal medicine to treat various disorders of the cardiovascular, respiratory, gastrointestinal, and central nervous systems. *Coleus forskolii* has also been used to help maintain weight loss and manage overall body weight.

Vitamin B12

Vitamin B12, also called cobalamin, is a water-soluble vitamin that has a key role in the normal functioning of the brain and nervous system, and the formation of red blood cells. It is one of eight B vitamins, and is involved in the metabolism of cells of the human body. Vitamin B12 specifically affects DNA synthesis, fatty acid and amino acid metabolism, and is used to treat vitamin B12 deficiency, cyanide poisoning, and the hereditary deficiency of transcobalamin II. Vitamin B12 is an ingredient in multi-vitamin pills and is a common ingredient in energy drinks and energy shots.

Red Beet Extract (*Beta vulgaris rubra*)

Red beet extract has been used as a natural medicine. Recent studies have provided evidence that beetroot ingestion offers beneficial physiological effects that may translate to improved clinical outcomes for several pathologies, including, hypertension, atherosclerosis, type 2 diabetes and dementia. A bioactive in beetroot is nitrate. The nitrate from beetroot has been shown to increase microcirculation and exercise performance. Supplementation with nitrate appears to reduce the oxygen cost of exercise and increase $VO_2$ max without altering exercise performance. Also present in beetroot are betalains, which may contribute its bioactivity and provide beneficial effects.

L-Arginine Nitrate ($NO_3$)

L-arginine is a known metabolic precursor to nitric oxide (NO). Such precursors are also called nitrovasodilators. Arginine is a semi-essential amino acid having the chemical name 2-amino-5 guanidinovaleric acid. The "L" form designation is used to identify the physiologically active form of the amino acid.

L-arginine may play a role in the treatment of heart disease due to its potential ability to block arterial plaque buildup, blood clots, platelet clumping, and to increase blood flow through the coronary artery. L-arginine is commonly sold as a health supplement for improving vascular health and treating erectile dysfunction in men.

Recent studies have suggested that dietary inorganic nitrate ($NO_3(—)$) supplementation may improve muscle efficiency and endurance exercise tolerance but possible effects during team sport-specific intense intermittent exercise have not been examined.

Combining L-arginine arginine and nitrate will provide a better NO boost, which results in an increase in blood flow and long lasting pumping effects to help with the muscle gains.

Tongkat ali (*Eurycoma longifolia*)

The *Eurycoma longifolia* plant is used in the traditional medicine of Indonesia, Malaysia and Vietnam. In Indonesia and Malaysia, the root of the plant is boiled in water, and the water is consumed as a health tonic for post-partum recovery, as an aphrodisiac, as well as a treatment for the relief of fever, intestinal worms, dysentery, diarrhea, indigestion, and jaundice. As a supplement, tongkat ali has been marketed for sexual health improvement, as an energy and stamina booster, for improving blood circulation, and as a testosterone booster.

Fenugreek (*Trigonella foenum-graecum*)

Fenugreek is a popular herb in Arabic regions and India, belonging to the family Fabaceae, it has been cultivated as a food crop in India, the Mediterranean region, North Africa and Yemen. Extracts of Fenugreek can be obtained from both the seeds and the fruit of the plant. Fenugreek has traditionally been used to enhance libido and masculinity. Fenugreek has also been used to alleviate blood sugar metabolism problems like diabetes. Fenugreek's contains at least two ingredients that are believed to provide health benefits, saponins and 4-hydroxyisoleucine. 4-hydroxyisoleucine has been shown to help normalize glucose metabolism and to have a positive effect on insulin resistance associated with obesity. Avalos-Coriano, A. et al, "4-Hydroxyisoleucine from Fenugreek (*Trigonella foenum-graecum*): Effects on insulin resistance Associated with obesity" *Molecules*, 2016, 21, p. 1596. Using in vivo studies, fenugreek has been shown to be helpful in reducing plasma glucose levels, increasing the level of lipid peroxidation, decreasing membrane fluidity, decreasing plasma triglyceride gain induced by oil administration, and reducing body weight gain induced by a high fat diet. Moreover, fenugreek has demonstrated positive impacts on combating oxidative stress resulting in a trend to lower oxidative modification of LDL.

Fenugreek also includes a variety of different saponins, which have hypocholesterolemic and antifungal activity, as well as help enhance the intake of food. Further, the seeds of fenugreek (*Trigonella foenum graecum* L.) are traditionally assumed to have restorative properties due to the saponin content. In addition Fenugreek contains testosterone-like components which are believed to promote bodily testosterone production and lean muscle build up.

Tribulus terrestris Extract

*Tribulus terrestris* is an herb from Ayurveda medicine that is mostly recommended for male health including virility and vitality, and its uses are directed towards cardiovascular and urogenital health. It is a common supplement for libido enhancing properties and testosterone boosting properties. A specific component, tribulosin, appears to have cardio-protective properties.

It is an object of certain embodiments of the present invention to provide a nutritional supplement that can be taken prior to exercise that causes a user to feel stronger, more energetic, and allows the user to exercise for a longer time. Such a supplement should improve exercise performance by increasing blood flow, oxygen consumption, calories burned per minute, and heart rate.

It is a further object of certain embodiments of the present invention to provide a pre-workout supplement made from natural herbs that is well-tolerated by the user.

These and other objects of the present invention will be apparent from the summary and detailed description of the invention, which follow.

SUMMARY OF THE INVENTION

In a first embodiment, the present invention relates to a nutritional product for improving performance during physical activity. The nutritional product includes *Rhodiola* root extract, French pine extract, *Pulsatilla vulgaris* extract, ginger extract, yohimbe extract, *Ginseng* extract, *Coleus forskohlii* extract, vitamin $B_{12}$, red beet extract, and arginine nitrate, tongkat ali, a combination of Fenugreek A (standardized to 4-Hydroxyisoleucine content) and Fenugreek B (standardized to saponins content), and *Tribulus terrestris* extract.

In the forgoing embodiment, the nutritional product may contain from about 50 mg to about 75 mg of *Rhodiola* root extract. The nutritional product of each of the forgoing embodiments may also contain from about 15 mg to about 25 mg of French pine extract.

In each of the forgoing embodiments, the nutritional product can contain from about 3.8 mg to about 8.8 mg of *Pulsatilla vulgaris* extract. The nutritional product of each of the forgoing embodiments may also contain from about 10 mg to about 35 mg of ginger extract. Each of the forgoing embodiments of the nutritional product may also contain from about 65 mg to about 90 mg of yohimbe extract.

In each of the above listed embodiments, the nutritional product may include from about 15 mg to about 30 mg of *Ginseng* extract. The nutritional product of each of the above embodiments may include from about 4 mg to about 10 mg of *Coleus forskohlii* extract. Each of the forgoing embodiments of the nutritional product may contain from about 0.10 mg to about 0.35 mg of Vitamin $B_{12}$.

From about 10 mg to about 25 mg of red beet extract may be included in the nutritional products of each of the forgoing embodiments. From about 250 mg to about 375 mg of arginine nitrate may be contained in each of the forgoing embodiments of the nutritional product. The nutritional product of each of the forgoing embodiments may contain from about 50 mg to about 80 mg of tongkat ali.

In each of the forgoing embodiments, the nutritional product may include from about 40 mg to about 50 mg of fenugreek A, in combination with, or in the absence of about 250 mg to about 350 mg of fenugreek B. The nutritional product of each of the forgoing embodiments may contain from about 50 mg to about 75 mg of *Tribulus terrestris* extract.

In each of the forgoing embodiment, when the nutritional product is ingested by a user, it provides an improvement in one or more of the following: oxygen consumed, respiratory rate, oxygen pulse %, calories burned, fat calories burned, maximum oxygen consumed, energy expenditure, heart rate, rate of perceived exertion, and the user's subjective view of the physical activity, as compared to the same user that has not ingested the nutritional product.

Another embodiment of the present invention is a method for improving a user's physical activity performance comprising the step of orally consuming an effective amount of a nutritional product of each of the forgoing embodiments to improve the user's physical activity performance. Preferably, the step of orally consuming the nutritional product occurs 60 to 90 minutes prior to initiation of physical activity.

Yet another embodiment of the invention is method for improving a user's physical activity performance comprising the step of orally consuming an effective amount of a nutritional product of each of the forgoing embodiments wherein the nutritional product is in the form of a first capsule and a second capsule and the first and second capsules are consumed 60 to 90 minutes prior to initiation of physical activity.

DETAILED DESCRIPTION OF THE PREFERRED EMBODIMENTS

In a first aspect, the present invention relates to a nutritional composition to be ingested prior to exercise to increase the performance of the user during exercise. Increased performance can be based on the subjective feelings of the user prior and during exercise, or can be based on a physiological response in the body. Specific physiological functions that are known to be beneficial to performance during physical activity include increases in blood flow, oxygen consumption, calories burned per minute, and a decreased heart rate. Such benefits can be obtained by ingestion of a nutritional product prior to physical exertion.

The nutritional product may comprise one or more components including a variety of herbal extracts, vitamins and amino acids. Each of *Rhodiola* root extract, French pine extract, *Pulstilla vulgaris* extract, ginger extract, yohimbe extract, *Ginseng* extract, *Coleus forskohlii* extract, vitamin B12, red beet extract, L-Arginine $NO_3$, tongkat ali, a combination of two different fenugreek extracts, and *Tribulus terrestris* extract contain ingredients which may provide some beneficial effect during physical activity. It has been found that the combination of these components may provide one or more substantial beneficial effects during physical activity.

The first ingredient of the nutritional product may be *Rhodiola* root extract. *Rhodiola* root extract is obtainable from the *Rhodiola rosea* plant that belongs to the Crassulaceae family. The extract of *Rhodiola* root typically includes the following compounds: Phenylpropanoids: rosavin, rosin, rosarian; Phenylethanol derivatives: salidroside (rhodioloside), tyrosol; Flavanoids: rodiolin, rodionin, rodiosin, acetylrodalgin, tricin; Monoterpernes: rosiridol, rosaridin; Triterpenes: daucosterol, beta-sitosterol; and Phenolic acids: chlorogenic and hydroxycinnamic, gallic acids. Extracts of *Rhodiola* are standardized to 3 percent or higher of rosavins and 1 percent or higher of salidroside, preferably the extract used in the compositions herein contains a minimum of 3 percent rosavins and 0.8-1 percent salidroside. *Rhodiola* root extract can be obtained commercially from different herbal extract suppliers in US.

In addition, or as an alternative to using an extract, *Rhodiola* root may be contained in the composition as a powder, as a combination of a plurality of the active compounds and mixtures thereof. For a particular active compound, for which a synthetic route is known, the active compound may be obtained synthetically.

Another ingredient of the nutritional product may be an extract from the French maritime pine. French Pine extract is obtainable from the *Pinus pinaster* species of plants that belong to the Pinaceae family. Any appropriate method can be used to prepare French Pine extract. For example, French Pine extract can be made using any suitable extraction process known in the art, for example the process as described in U.S. Pat. No. 4,698,360. Such extracts can be standardized based on the extraction ratio, for example, 1000:1 i.e. 1000 parts pine bark to extraction media. Preferably, this ratio of pine bark to extraction media is used.

French Pine extract can be obtained commercially from European herbal extract suppliers.

Extract from *Pulsatilla vulgaris* may also be a component of the nutritional product. *Pulsatilla Vulgaris* extract is obtainable from the *Pulsatilla Vulgaris* species of plants that belong to the Ranunculaceae family. Any appropriate method can be used to prepare *Pulsatilla Vulgaris* extract. For example, *Pulsatilla Vulgaris* extract can be made by distillation of the plant or a portion thereof with water. Such extracts can be standardized to, for example, 70 percent polyphenols. Preferably, the extract contains at least 10 percent of polyphenols. In some cases, *Pulsatilla Vulgaris* extract can be obtained commercially from different herbal extract suppliers in the US or Europe.

The fourth ingredient of the nutritional product may be obtained from ginger (also commonly called ginger root). Ginger contains 1-4% essential oil (oleoresin). The active compounds of ginger which may be employed in the nutritional product include, but are not limited to, 1,8-cineole, 10-dehydrogingerdione, 10-gingerol, 6-gingerdione, 6-gingerol, 6-shogaol, 8-β-17-epoxy-λ-trans-12-ene-15,16-diol, 8-gingerol, 8-shogaol, 9-oxo-nerolidol, acetaldehyde, acetic acid, alanine, α-linolenic-acid, α-linolenic acid, α-phellandrene, α-piene, α-terpinene, α-terpineol, α-zingiberene, ar-curcumene, arginine, ascorbic acid, asparagine, β-bisabolol, β-carotene, β-elemene, β-eudesmol, β-ionone, β-myrcene, β-phellandrene, β-pinene, β-selinene, β-sesquiphellandrene, β-sitosterol, (β-thujone, bornyl-acetate, boron, caffeic acid, calcium, camphene, camphor, capric acid, caprylic acid, capsaicin, caryophyllene, chavicol, chlorogenic acid, chromium, citral, citronellal, citronellal, cobalt, copper, cumene, curcumin, cystine, delphinidin, δ-cadinene, elemol, ethyl acetate, ethyl-myristate, farnesal, farnesene, ferulic acid, furfural, γ-aminobutyric acid, γ-terpinene, geranial, geraniol, geranyl-acetate, gingerenone, glutamic acid, glycine, hexahydrocurcumin, histidine, isogingerenone-B, isoleucine, kaempferol, lecithin, limonene, linoleic acid, magnesium, manganese, methionine, mufa, myrecene, myricetin, myristic acid, neral, nerol, nerolidol, niacin, nickel, oleic acid, oxalic acid, p-coumaric acid, p-cymene, p-hydroxy-benzoic acid, palmitic acid, pantothenic acid, paradol, patchoulic alcohol, phenylalanine, quercetin, riboflavin, selenium, shikimic-acid, terpinen-4-ol, thiamin, tryptophan, vanillic acid, vanillin, zinc, and zingerone. Also, mixtures of two or more of these active compounds may be employed.

Ginger, can be incorporated in the nutritional product in many different forms including ginger extract, ginger powder, one or more active compounds of ginger and mixtures thereof. Also, for any specific active compound of ginger for which suitable synthesis routes are known, the active compound can be prepared synthetically. Preferably, the fourth ingredient is included in the composition as an extract of ginger.

Any appropriate method can be used to prepare ginger extract. For example, ginger extract can be made by hydrodistillation, steam distillation, leaching, solvent extraction, pressing and extraction with supercritical carbon dioxide. Such extracts can be standardized to, for example, at least 5% gingerols. Preferably, the extract contains at least 5 percent of gingerols.

Another ingredient of the nutritional product may be obtained from Yohimbe extract. Yohimbe extract is obtainable from the *Pausinystalia johimbe* plant that belongs to the Rubiaceae family. The primary active ingredient is considered to be yohimbine. Yohimbe can be included in the composition in many different forms. Those different forms include bark powder, bark extract, or as one or more active compounds of yohimbe and mixtures thereof. For a particular active compound, for which a synthetic route is known, the active compound may be obtained synthetically. Preferably, yohimbe bark extract is used in the composition. The yohimbe bark extract can be obtained using any suitable extraction process known in the art, for example through the use of water or alcohol. Such extracts can be standardized to, for example, 2-20% yohimbines. Preferably, the extract contains at least 9 percent yohimbines. Yohimbe bark extract can be obtained commercially from different herbal extract suppliers in the US and Europe.

The nutritional product also contains *Ginseng* extract. *Ginseng* extract is obtainable from the *Panax ginseng* plant that belongs to the Araliaceae family. The active compounds of *Ginseng* which may be useful in the present invention include, but are not limited to, over 100 different components collectively referred to as ginsenosides, which include steroid-like saponins, falcarinol, falcarintriol, acetic acid, linolenic acid, and microRNAs, as well as mixtures of two or more of these compounds. The primary active ingredient of *Ginseng* is considered to be a combination of a plurality ginsenosides.

*Ginseng* can be included in the nutritional product in the form of an extract or root powder. Any appropriate method known in the art can be used to prepare *Ginseng* extract. For example, *Ginseng* extract can be made using water/alcohol tinctures, or by grinding up the root. Extracts can be standardized to, for example, 1% to 50% ginsenosides. Preferably *Ginseng* extract contains at least 10% ginsenosides. In some cases, *Ginseng* extract can be obtained commercially from different herbal extract suppliers in the US and Europe.

Another ingredient of the nutritional product is *Coleus forskohlii* extract. *Coleus forskohlii* extract is obtainable from *Plectranthus barbatus* plants that belong to the Lamiaceae family. The primary active ingredient in *Coleus forskohlii* extract is considered to be forskolin.

Any appropriate method can be used to prepare a *Coleus forskohlii* extract. For example, *Coleus forskohlii* extract can be made using an ethanol or hydroalcoholic extraction. Such extracts can be standardized to, for example, 10% to 20% forskolin. A preferable *Coleus forskohlii* extract contains at least 10% forskolin. In some cases, *Coleus forskohlii* extract can be obtained commercially from different herbal extract suppliers in the US and Europe.

Vitamin B12 (cobalamin) can also be included in the nutritional product. Vitamin B12 is available commercially from many different sources.

Another ingredient that can be used in the nutritional product is red beet extract also referred to as beetroot extract, or red beetroot extract. Beetroot extract can be obtained from *Beta vulgaris* subspecies vulgaris (conditiva group) plants. The active ingredients in beetroot extract may include, nitrates, betalains (a group of phenolic metabolites, including Betanin), hydroxycinnamic acids such as gallic, syringic, and caffeic acids, and flavonoids. Each of these ingredients are thought to provide some health benefits. The primary active ingredients are thought to be the nitrates or the betalains, such as betanin. As such, beetroot extract may be standardized to either of these active compounds. For example, beetroot extract tends to be dosed on the nitrate content, with around 0.1-0.2 mmol/kg (6.4-12.8 mg/kg) being the target for nitrate dosing.

Alternatively, or in addition to nitrate content, beetroot extract can be standardized to the amount of betanin. A preferred beetroot extract contains at least 0.3% betanins. In some cases, beetroot extract can be obtained commercially from different herbal extract suppliers in the US and Europe.

Another component of the nutritional product is L-Arginine $NO_3$. L-Arginine is the physiologically active form of an essential amino acid having the chemical name 2-amino-5 guanidinovaleric acid. L-Arginine $NO_3$ combines one molecule of arginine and a nitrate group connected by a hydrogen bond. L-Arginine $NO_3$ is thought to prolong vasodilation more than L-arginine alone. L-Arginine $NO_3$ is available as a powder and can be obtained commercially from different suppliers in the US.

Preferably, the L-Arginine in the composition is free of other amino acids, peptides and proteins that would interfere with the uptake of L-Arginine.

The nutritional product also contains Tongkat Ali, which is also known as *Eurycoma Longifolia* Jack. Tongkat ali is obtainable from the plant family of Simaroubaceae with *Eurycoma* being the family, and the *Longifolia* species being used for medicinal purposes. The active compounds of Tongkat ali which may be useful in the nutritional product include, but are not limited to, over 150 different varieties of quassinoids, Eurycolactones, Canthin-6-one metabolites, Eurylene and teurilene, 23,24,25-trihydroxytirucall-7-en-3, 6-dione, Eurypeptides, and Glycosaponins, as well as mixtures of two or more of these compounds. The primary active ingredient of Tongkat ali is considered to include one or more of, eurycomanol, eurycomanone, and eurycomalactone.

Tongkat ali can be included in the present product in the form of an extract or root powder. Any appropriate method known in the art can be used to prepare tongkat ali extract. For example, tongkat ali extract can be made using water or alcohol extraction. Extracts can be standardized to, for example, 1% to 50% eurycomanone. Preferably tongkat ali extract contains at least 10% eurycomanone. In some cases, tongkat ali extract can be obtained commercially from different herbal extract suppliers in the US and Europe.

Fenugreek Blend of Fenugreek A and Fenugreek B

Additional ingredients contained in the nutritional product are fenugreek A, standardized to 4-Hydroxyisoleucine content, and fenugreek B, standardized to saponins content. Fenugreek extract is obtainable from the seeds and/or the fruit of the plant *Trigonella foenum-graecum* L. The active compounds of fenugreek, which may be useful in the present invention include, but are not limited to, various different saonins and 4-hydroxyisoleucine. Numerous other ingredients in fenugreek extract may also provide beneficial effects on, including protocatechuic acid, quinic acid, gallic acid, vitamin C, and several different minerals.

Fenugreek can be included in the present product in the form of seed or fruit extract. Any appropriate method known in the art can be used to prepare fenugreek extract. For example, fenugreek extract can be made using water or ethyl acetate extraction, with ethyl acetate extraction being preferred for having higher antioxidant properties. Extracts can be standardized to, for example, >10% 4-Hydroxyisoleucine or >50% saponins. Preferably, fenugreek extract contains a combination of Fenugreek A, which contains at least 20% 4-Hydroxyisoleucine and Fenugreek B, which contains 60% saponins. The two different Fenugreek extracts are preferably combined into a single fenugreek extract with a ratio for the combinations of Fenugreek B:Fenugreek A preferably ranging from about 1:8 to about 2:7. Most preferably the ratio of Fenugreek B to Fenugreek A is 1.27:8.73. In some cases, fenugreek extract can be obtained commercially from a US or European supplier.

Another ingredient contained in the nutritional product is *Tribulus terrestris* extract. *Tribulus terrestris* extract is obtainable from the *Tribulus terrestris* plant of the family Zygophyllaceae. The active compounds of *Tribulus terrestris* extract, which may be useful in the present invention include, but are not limited to, Protodioscin, Pseudoprotodioscin, Dioscin and Diosgenin, Tribulosin, Hecogenin-3-O-β-d-glucopyranosyl(1→4)-β-d-galactopyranoside, Protodibestin and tribestin, spirstanol and furostanol saponins, di-p-coumaroylquinic acid and 4,5-di-p-cis-coumaroylquinic acid, and vitamin C, as well as mixtures of two or more of these compounds. The primary active ingredient is considered to include one or both protodioscin and tribulosin.

*Tribulus terrestris* extract can be included in the present product in the form of an extract or root powder. Any appropriate method known in the art can be used to prepare *Tribulus terrestris* extract. For example, *Tribulus terrestris* extract can be made using water or ethanol extraction. Extracts can be standardized to, for example, 5% and 20% total protodioscins. Preferably, *Tribulus terrestris* extract contains at least 2.5% protodioscin. In some cases, *Tribulus terrestris* extract can be obtained commercially from US and European suppliers.

All active compounds of the present invention may be obtained from other sources, if available. Thus, the phrases "is obtainable from," "which can be obtained from," or "which may be obtained from" is meant to encompass compounds or compositions that are obtainable from the listed plant source, but also encompass synthetic forms of the same compounds and/or compositions as well as the same compounds and/or compositions obtained from other sources.

The ingredients of the composition of the present invention, which may be obtained from the sources listed above, can preferably be used in the forms of an extract. One suitable general extraction procedure is described below.

The extraction procedure comprises, generally, the steps of:

1) cleaning the plant from which the pharmacologically or biologically active plant extract has to be obtained to remove any foreign matter thereon;
2) particulating the plant to obtain a particulate mass having particle size ranging from 0.001 to about 10 $mm^3$; and
3) subjecting the particulate mass to at least one polar and at least one non-polar solvent to obtain separate fractions of the plant extract soluble in the respective solvents, and mixing the fraction so obtained to obtain the plant extract in accordance with this invention.

For instance, in the case of ginger, the process comprises the steps of:

1) cleaning the roots of ginger to remove any foreign matter thereon;
2) particulating the roots to obtain a particulate mass having particle size ranging from 0.001 to about 10 $mm^3$;
3) subjecting the particulate mass to distillation to obtain a volatile fraction, if any, from the particulate mass;
4) cooking the distilled particulate mass in a polar solvent, such as water to soluble material in the distillation-treated particulate mass to obtain a first solution and a first residue;
5) filtering the first solution from the first residue;
6) evaporating the filtrate obtained from the first solution to remove the solvent and obtain a solute designated as fraction A from the particulate mass;
7) subjecting the first residue to treatment with a second polar solvent such as 25% to 99% ethanol for twelve to thirty-six hours to obtain a second solution and a second residue;

8) filtering the second solution from the second residue to obtain a second filtrate;
9) evaporating the second filtrate to remove its solvent and obtain a solute designated as fraction B from the particulate mass;
10) subjecting the second residue to less polar or non-polar solvents; such as petroleum ether, for twelve to thirty-six hours to obtain a third solution and a third residue, and filtering the third solution from the third residue to obtain a third filtrate;
11) evaporating the third filtrate to remove its solvent and obtain a solute designated as fraction C from the particulate mass; and
12) homogeneously mixing the volatile fraction, with fractions A, B and C from the particulate mass to obtain a plant extract.

The process is suitable for the preparation of a pharmacologically or biologically active plant extracts substantially in a convenient administrable dosage form from the plants mentioned above.

Solvents useful for extracting plant material include water, ethanol, propanol, paraffin, hexane, petroleum ether, toluene, acetone, methyl ethyl ketone, and other common organic solvents. Water, ethanol, acetone and petroleum ether are the preferred solvents for use in plant extraction.

Alternatively, powders, and/or one or more of the active compounds contained therein can be purchased from commercial sources such as the sources listed above.

Alternatively, the product of the present invention may include two distinct compositions included in two different capsules that are taken by a user at two different times.

Table A shows the range of amounts for each of the above extracts that are contained within each gram of the nutritional product.

TABLE A

| Ingredients | Total Amount in Product | Preferred Total Amount/dose mg/dose |
| --- | --- | --- |
| *Rhodiola* Root extract | 50 mg-75 mg | 65-73 |
| French Pine extract | 15 mg-25 mg | 17-20 |
| *Pulsatilla* | 3.8 mg-8.8 mg | 3.5-7 |
| Ginger extract | 10 mg-35 mg | 25-32 |
| Yohimbe extract | 65 mg-90 mg | 75-85 |
| Korean Ginseng extract | 15 mg-30 mg | 20-25 |
| *Coleus Forskohlii* extract | 4 mg-10 mg | 5-8 |
| Vitamin B12 | 0.10 mg-0.35 mg | 0.15-0.25 |
| Red Beet Extract | 10 mg-25 mg | 15-20 |
| L-Arginine NO3 | 250 mg-375 mg | 300-385 |
| TONGKAT ALI | 50 mg-80 mg | 68-78 |
| Fenugreek B (60% Saponins) | 40 mg-50 mg | 40-45 |
| Fenugreek A (20% 4-Hydroxyisoleucine) | 250 mg-350 mg | 270-300 |
| *Tribulus terrestris* X | 50 mg-75 mg | 50-60 |

The compositions of the present invention may also be formulated with a pharmaceutically acceptable carrier. The pharmaceutically acceptable carrier includes but is not limited to: (a) carbohydrates including fructose, sucrose, sugar, dextrose, starch, lactose, maltose, maltodextrins, corn syrup solids, honey solids, and commercial tableting compositions, (b) sugar alcohols including mannitol, sorbitol, xylitol, and (c) various relatively insoluble excipients including dicalcium phosphate, calcium sulfate, calcium carbonate, microcrystalline cellulose and other pharmaceutical tableting ingredients.

Additional ingredients that may provide health benefits may also be included in the above compositions. Such additional ingredients are not limited to, but may include, epimedium extract, maca pure extract, and zinc gluconate. One or more of these optional ingredients may be included in the compositions according to amounts shown in Table B.

TABLE B

| Ingredients | Total Amount in Product | Preferred Total Amount/dose mg/dose |
| --- | --- | --- |
| Epimedium extract | 6.0 mg-10 mg | 7.5-9.0 |
| Maca Pure extract | 3.0 mg-12.5 mg | 3-9 |
| Zinc gluconate | 45 mg-85 mg | 50-60 |

Preferably, the compositions of the present invention may be formulated in any orally acceptable dosage form including, but not limited to, capsules, tablets, lozenges, troches, hard candies, powders, sprays, elixirs, syrups, and suspensions or solutions. In the case of tablets, for oral use, the pharmaceutically acceptable carrier may further include lactose and corn starch. Lubricating agents may also be added to the tablets, including, for example, magnesium stearate, sodium lauryl sulfate and talc. Tablets may also contain excipients such as sodium citrate, calcium carbonate and calcium phosphate. Disintegrants such as starch, alginic acid and complex silicates, may also be employed. Tablets may also include binding agents such as polyvinylpyrrolidone, gelatin, PEG-8000 and gum acacia.

Alternatively, the composition of the present invention may be formulated in liquid form, such as syrups, mouthwashes or sprays with a solvent or dispersant such as water, or other liquids in a pharmaceutically acceptable carrier.

The composition may also be formulated in chewable compositions such as soft candy, gum drops, liquid filled candies, chewing gum bases and dental supplies, such as toothpastes and mouthwashes by further including fructose, sucrose, or saccharin in the composition, as needed.

The composition of the invention may be formulated in capsule form with or without diluents. For capsules, useful diluents include lactose and dried corn starch. When suspensions are employed, emulsifying and/or suspending agents may be employed in the suspensions.

Other materials which may optionally be included in the compositions of the present invention include inositol, other B-complex vitamins, and anti-inflammatories. Also, ingredients such as sweeteners, flavorants, coloring agents, dyes, and diluents such as water, ethanol, propylene glycol, glycerin and various combinations thereof, may be included in the compositions of the present invention.

The optional sweeteners which may be used in the compositions of the present invention include, but are not limited to, saccharin, aspartame, cyclamates, acesulfame K, neohesperidin dihydrochalcone, other super sweeteners, and mixtures thereof, which may be added to the carrier in amounts sufficiently low so as not to chemically interact with the main ingredients of the composition.

The optional flavorants which may be used in the compositions of the present invention include, but are not limited to, peppermint, peppermint-menthol, eucalyptol, wintergreen, licorice, clove, cinnamon, spearmint, cherry, lemon, orange, lime, menthol and various combinations thereof.

In general, the primary ingredients shown above in Table A, make up from about 78-98 by weight of the total composition. Preferably, the main ingredients will make up 90% by weight of the total composition. More preferably, the main ingredients make up 95% by weight of the total composition.

In a second aspect, the present invention relates to a method of using a nutritional product to enhance the exercise performance of a user.

The method of the present invention involves the ingestion or oral intake of a nutritional product of the present invention prior to physical activity. Preferably, the user will ingest the capsule approximately 30-90 minutes prior to physical activity, more preferably, the nutritional product is taken approximately 60-90 minutes prior to physical activity.

In an alternative method, two capsules are used for the ingestion or oral intake of a nutritional product of the present invention prior to physical activity. For such use, the user will ingest two separate capsules the first capsule containing at least a first composition and the second capsule containing at least a second composition. The first and the second compositions are preferably not identical to each other. Each capsule is preferably taken approximately 30-90 minutes prior to physical activity, more preferably, each capsule is taken approximately 60-90 minutes prior to physical activity.

The effective amount of the composition will vary depending on such factors as the user, the particular mode of administration, the activity of the particular active ingredients employed, the age, bodyweight, general health, sex and diet of the user, time of administration, the particular combination of ingredients employed, the total content of the main ingredient of the composition, and the desired effect. It is within the skill of the person of ordinary skill in the art to account for these factors.

The composition may be administered prior to physical activity, as often as a user exercises, or as needed. As discussed above, the composition of the present invention may be administered to a user in any orally acceptable dosage form including, but not limited to tablets, capsules, lozenges, troches, hard candies, powders, sprays, elixirs, syrups, and suspensions or solutions.

The method of the present invention provides improved physical activity performance, including increased endurance and improved blood flow.

The invention will be further illustrated by the examples given below which are not to be construed as limiting the invention in any way.

EXAMPLES

Example 1 A Product of the Present Invention

A nutritional product of the present invention was formulated in the form of capsules. The ingredients of the capsules are listed below. The active ingredients are shown in Table C.

TABLE C

| Ingredients | Targeted Amount/dose mg/dose |
|---|---|
| *Rhodiola* Root extract | 65-73 |
| French Pine extract | 17-20 |
| *Pulsatilla vulgaris* extract | 3.5-7 |
| Ginger extract | 25-32 |
| Yohimbe extract | 75-85 |
| Korean Ginseng extract | 20-25 |

TABLE C-continued

| Ingredients | Targeted Amount/dose mg/dose |
|---|---|
| *Coleus Forskohlii* extract | 5-8 |
| Vitamin B12 | 0.15-0.25 |
| Red Beet Extract | 15-20 |
| L-Arginine NO3 | 300-385 |
| TONGKAT ALI | 68-78 |
| Fenugreek 52 | 40-45 |
| Fenugreek 7 | 270-300 |
| *Tribulus terrestris* X | 50-60 |

Other ingredients contained in the composition of this example are shown in Table D.

TABLE D

| Ingredients | Targeted Amount/dose mg/dose |
|---|---|
| Epimedium extract | 7.5-9.0 |
| Maca Pure extract | 3-9 |
| Zinc gluconate | 50-60 |

Example 2 Objective Measurement of Improved Performance

A selected number of users that participate in physical activity may be used to conduct a clinical study. A Double-Blind, Randomized, Placebo-Controlled Clinical Study was designed to evaluate the Efficacy of Oral Products on Exercise Endurance and Energy in Healthy Subjects. A total number of 64 subjects age 25-55 years old completed the study. Measurements were made to determine the extent that the use of the nutritional product of the present invention improves physical activity endurance, is safe and well tolerated, and provides perceived benefits to the user. Subjects were instructed to take the two capsules 90 minutes prior to exercise and measurements of one or more of the following parameters may be taken of the subject to show that the nutritional product improves physical activity performance:

Additionally, physiological parameters were monitored to ensure that the product is safe and well tolerated. The results were compared to the results from the placebo treatment group.

Example 3 Subjective Measurement of Improved Performance

A selected number of users that participate in physical activity may be used to conduct a clinical study. Subjects may be instructed to take the capsules 90 minutes prior to physical activity, and after physical activity is complete, a questionnaire may be provided to the subjects to determine their subjective perception of the product and its effect on physical activity performance. The answers to the questionnaire can be used to determine that after use of the products the subjects felt, stronger, more energetic, that they can do more, reduced shortness of breath, can perform physical activity for longer, and feel less tired.

Changes may be made in carrying out the methods and to the compositions of the invention above set forth above without departing from the spirit and scope of the invention. It is intended that all matter contained in the above description shall be interpreted as illustrative and not in a limiting sense. The scope of this invention is to be determined from the claims appended hereto. The responses may be compared to responses from the placebo treatment group.

The Energy and Endurance Blend product showed statistically significant favorable responses and outperformed the placebo product at the Treadmill Challenge and product evaluations for the following statements:

I feel stronger.
I feel more energetic.
I feel less shortness of breath.
I feel like I have more energy.
I feel like I can work out/exercise longer.
The product worked the first time.
The product worked every time I used it.
I would recommend this product to my friends.
Perceived rate of exertion reached during the Treadmill Challenge.

We claim:

1. A method for improving a user's physical activity performance comprising the step of orally consuming an effective amount of a nutritional product to improve the use's physical activity performance, wherein said nutritional product comprises:

Rhodiola root extract, French pine extract, *Pulsatilla*, ginger extract, yohimbe extract, *Ginseng* extract, *Coleus forskoblii* extract, Vitamin B12, red beet extract, L-Arginine $NO_3$, tongkat ali, a combination of fenugreek A and fenugreek B, and *Tribulus terrestris* extract, and wherein the nutritional product comprise from about 250 mg to about 375 mg of the L-Arginine $NO_3$ per dose, and the fenugreek A is a fenugreek extract comprising >10 wt. % 4-hydroxyisoleucine and the fenugreek B is a fenugreek extract comprising >50 wt. % t saponins.

2. The method as claimed in claim 1, wherein the step of orally consuming the nutritional product occurs 60 to 90 minutes prior to initiation of physical activity.

3. A method for improving a user's physical activity performance comprising the step of orally consuming an effective amount of a nutritional product comprising: *Rhodiola* root extract, French pine extract, *Pulsatilla*, ginger extract, yohimbe extract, *Ginseng* extract, *Coleus forskohlii* extract, Vitamin B12, red hut extract, L-Arginine $NO_3$, tongkat ali, a combination of fenugreek A and fenugreek B, and *Tribulus terrestris* extract, wherein the nutritional product comprises from about 250 mg to about 375 me of the L-Arginine $NO_3$ per dose, and the fenugreek A is a fenugreek extract comprising >10 wt. % 4-hydroxyisoleucine and the fenugreek B is a fenugreek extract comprising >50 wt. % saponins, said nutritional product is encapsulated in a first capsule and a second capsule, and the first and second capsules are consumed 60 to 90 minutes prior to initiation of physical activity.

4. The method as claimed in claim 3, wherein the composition of the nutritional product in the first capsule is a first composition of the nutritional product in the second capsule is a second composition.

5. The method as claimed in claim 1, wherein the nutritional product, when ingested by a user, provides an improvement in one or more of the following: oxygen consumed, respiratory rate, oxygen pulse %, calories burned, fat calories burned, maximum oxygen consumed, energy expenditure, heart rate, rate of perceived exertion, and the user's subjective view of the physical activity, as compared to a same user that has not ingested the nutritional product.

6. The method as claimed in claim 1, wherein the nutritional product comprises from about 50 mg to about 75 mg of the *Rhodiola* root extract.

7. The method as claimed in claim 1, wherein the nutritional product comprises from about 15 mg to about 25 mg of the French pine extract.

8. The method as claimed in claim 1, wherein the nutritional product comprises from about 10 mg to about 35 mg of the ginger extract.

9. The method as claimed in claim 1, wherein the nutritional product comprises from about 65 mg to about 90 mg of the yohimbe extract.

10. The method as claimed in claim 1, wherein the nutritional product comprises from about 15 mg to about 30 mg of the *Ginseng* extract.

11. The method as claimed in claim 1, wherein the nutritional product comprises from about 4 mg to about 10 mg of the *Coleus forskohlii* extract.

12. The method as claimed in claim 1, wherein the nutritional product comprises from about 0.10 mg to about 0.35 mg of the Vitamin B12.

13. The method as claimed in claim 1, wherein the nutritional product comprises from about 10 mg to about 25 mg of the red beet extract.

14. The method as claimed in claim 1, wherein the nutritional product comprises from about 50 mg to about 80 mg of the tongkat ali.

15. The method as claimed in claim 1, wherein the nutritional product comprises from about 40 mg to about 50 mg of the fenugreek A.

16. The method as claimed in claim 1, wherein the nutritional product comprises from about 250 mg to about 350 mg of the fenugreek B.

17. The method as claimed in claim 1, wherein the *Pulsatilla* is *Pulsatilla vulgaris* extract in a concentration of from about 3.8 mg to about 8.8 mg of the *Pulsatilla vulgaris* extract per dose.

18. The method as claimed in claim 3, wherein the nutritional product, when ingested by a user, provides an improvement in one or more of the following: oxygen consumed, respiratory rate, oxygen pulse %, calories burned, fat calories burned, maximum oxygen consumed, energy expenditure, heart rate, rate of perceived exertion, and the user's subjective view of the physical activity, as compared to a same user that has not ingested the nutritional product.

19. The method as claimed in claim 3, wherein the nutritional product comprises from about 50 mg to about 75 mg of the *Rhodiola* root extract.

20. The method as claimed in claim 3, wherein the *Pulsatilla* is *Pulsatilla vulgaris* extract in a concentration of from about 3.8 mg to about 8.8 mg of the *Pulsatilla vulgaris* extract per dose.

* * * * *